United States Patent
Lee et al.

(10) Patent No.: US 7,803,350 B2
(45) Date of Patent: Sep. 28, 2010

(54) RADIOACTIVE ARSENIC-CONTAINING COMPOUNDS AND THEIR USES IN THE TREATMENT OF TUMORS

(75) Inventors: Te-Wei Lee, Taipei (TW); Chun-Ying Huang, Taipei (TW); Ming-Shiuan Wu, Taipei (TW); Te-Jung Chen, Taoyuan (TW); Kwo-Ping Chang, Taoyuan (TW); Shiang-Rong Chang, Taoyuan (TW); Shyh-Yi Chyi, Taoyuan (TW); Chih-Hsien Chang, Hsinchu (TW); Yin-Mao Hsu, Taipei (TW); Kuo-Hsien Fan, Taichung (TW); Wei-Chuan Hsu, Miaoli (TW); Ying-Kai Fu, Taoyuan (TW); Charng-Feng Kao, Taipei (TW)

(73) Assignees: Institute of Nuclear Energy Research Rocaec, Taoyuan (TW); TTY Biopharm Company, Limited, Taipei (TW)

( * ) Notice: Subject to any disclaimer, the term of this patent is extended or adjusted under 35 U.S.C. 154(b) by 386 days.

(21) Appl. No.: 11/881,901

(22) Filed: Jul. 30, 2007

(65) Prior Publication Data

US 2008/0003177 A1    Jan. 3, 2008

Related U.S. Application Data

(62) Division of application No. 10/792,191, filed on Mar. 3, 2004, now abandoned.

(30) Foreign Application Priority Data

Apr. 23, 2003    (TW) ............................. 92109497 A

(51) Int. Cl.
*A61K 51/00* (2006.01)
*A61K 36/14* (2006.01)

(52) U.S. Cl. ............... 424/1.61; 424/1.11; 424/623; 424/620; 424/9.1

(58) Field of Classification Search ........... 424/1.11, 424/1.61, 1.81, 9.1, 620, 621, 623; 423/601, 423/617; 514/1; 600/1
See application file for complete search history.

(56) References Cited

U.S. PATENT DOCUMENTS

2004/0213737 A1    10/2004    Huang et al.

FOREIGN PATENT DOCUMENTS

WO    WO 99/24029    5/1999

OTHER PUBLICATIONS

Zhi-Xiang Shen et al, Use of Arsenic Trioxide ($As_2O_3$) in the Treatment of Acute Promyelocytic Leukemia (APL): II. Clinical Efficacy and Pharmacokinetics in Relapsed Patients, Blood, vol. 89, No. 9, May 1, 1997: pp. 3354-3360.

Zhen-Yi Wang, Arsenic Compounds as Anticancer Agents, Cancer Chemotherapy and Pharmacology, DOI 10.1007/s002800100309, Published Online: Nov. 27, 2001.
Shen Y et al., Studies on the Clinical Efficacy and Pharmacokinetics of Low-Dose Arsenic Trioxide in the Treatment of Relapsed Acute Promyelocytic Leukemia: A Comparison With Conventional Dosage, Leukemia 2001, May : 15(5): pp. 735-741.
Muto A. et al, A Novel Differentiation-Inducing Therapy for Acute Promyelocytic Leukemia With a Combination of Arsenic Trioxide and GM-CSF, Leukemia 2001, Aug: 15(8): pp. 1176-1184.
Guo-Qiang Chen et al., Use of Arsenic Trioxide ($As_2O_3$) in the Treatment of Acute Promyelocytic Leukemia (APL): I. $As_2O_3$ Exerts Dose-Dependent Dual Effects on APL Cells, Blood, vol. 89, No. 9, May 1, 1997, pp. 3345-3353.
Wilson H. Miller et al., Mechanisms of Action of Arsenic Trioxide[1], Cancer Research 62, Jul. 15, 2002, pp. 3893-3903.
Anthony J. Murgo, Clinical Trials of Arsenic Trioxide in Hematologic and Solid Tumors: Overview of the National Cancer Institute Cooperative Research and Development Studies, The Oncologist 2001; 6 (Suppl. 2), pp. 22-28.
Lin et al., Study on Anti-Tumor Activity of Arsenic Trioxide, China Journal of Chinese Materia Medica (1999), 24(3), pp. 1-3.
Meral Tayan Ercan et al., Therapeutic Radiopharmaceuticals, Current Pharmaceutical Design, 2000, 6., pp. 1085-1121.
Yong-Jin Chun et al., Enhancement of Radiation Response in Human Cervical Cancer Cells in Vitro and in Vivo by Arsenic Trioxide ($As_2O_3$), FEBS Letters 519, (2002), pp. 195-200.
Samir C. Mehta et al., Targeted Drug Delivery for Boron Neutron Capture Therapy, Pharmaceutical Research, vol. 13, No. 3, 1996, pp. 344-351.
Mehta et al., "Targeted Drug Delivery for Boron Neutron Capture Therapy", Pharmaceutical Research, 1996, vol. 13, No. 3, Plenum Publishing Corporation.
Brunet C et al., "Whole Body Auto Radiographic Study of the Distribution of Radioactivity in Pregnant Mice Given Arsenic-73 Labelled Arsenic Tri Oxide", Toxicological European Research, vol. 5, No. 2, 1983, pp. 55-62.

(Continued)

*Primary Examiner*—D L Jones
(74) *Attorney, Agent, or Firm*—The Webb Law Firm

(57) ABSTRACT

This invention provides a process for producing a radioactive arsenic-containing compound, comprising the steps of: (i) subjecting an arsenic-containing compound to a neutron irradiation treatment, said arsenic-containing compound being selected from a group consisting of $As_2O_3$, $As_2S_3$, $As_2S_2$, and a combination thereof, such that the arsenic element contained in the arsenic-containing compound is converted to a radioactive arsenic isotope; and (ii) recovering the resultant product from step (i).

This invention also provides a pharmaceutical composition comprising a therapeutically effective amount of the radioactive arsenic-containing compound and a pharmaceutically acceptable carrier. The pharmaceutical composition can be used in the treatment of tumors/cancers such as hematological malignancies and solid tumors.

13 Claims, 2 Drawing Sheets

OTHER PUBLICATIONS

Chun Yong Jin et al., "Enhancement of Radiation Response in Human Cervical Cancer Cells in Vitro and in Vivo by Arsenic Trioxide (As203)". FEBS Letters, May 22, 2002, vol. 519, No. 1-3, pp. 195-200.

ChemIDplus Advanced, Full Record of "Arsenic trioxide", http://chem.sis.nlm.nih.gov/chemidplus/jsp/common/ChemFull.jsp?MW=197.841, 2004.

Born et al., Naturwissenschaften, vol. 29, 1941, pp. 182-183.

Morrison, F.O. et al., "The Distribution of Radioactive Arsenic in the Organs of Poisoned Insect Larvae," Canadian Journal of Research, vol. 27, Sec. D, 1949, pp. 265-269.

Wang Z.Y., Cancer Chemother Pharmacol, 48 Suppl. 1, (2001), pp. S72-S76.

Lewis, R.J., Hawley's Condensed Chemical Dictionary, Twelfth Edition, 1993, p. 991.

Emran, Ali M. et al., "Synthesis and Identification of [$^{76}$AS]Arsenic Trichloride," Appl. Radiat. ISOT., vol. 37, No. 6, 1986, pp. 545-547.

RADIOACTIVE ARSENIC-CONTAINING COMPOUNDS AND THEIR USES IN THE TREATMENT OF TUMORS

CROSS REFERENCE TO RELATED APPLICATIONS

This application is a divisional application of co-pending U.S. patent application Ser. No. 10/792,191, filed Mar. 3, 2004, which is incorporated herein by reference and claims priority of Taiwan Patent Application No. 092109497, filed Apr. 23, 2003.

BACKGROUND OF THE INVENTION

1. Field of the Invention

This invention relates to a process for preparing a radioactive arsenic-containing compound and uses of the radioactive arsenic-containing compound in the treatment of tumors/cancers such as hematological malignancies and solid tumors. Particularly, an arsenic-containing compound selected from a group consisting of $As_2O_3$, $As_2S_3$, $As_2S_2$ and a combination thereof is subjected to a neutron irradiation treatment such that the arsenic element contained in the arsenic-containing compound is converted to a radioactive arsenic isotope. The radioactive arsenic-containing compound can be formulated into a pharmaceutical composition for the treatment of tumors/cancers, such as hematological malignancies and solid tumors.

2. Description of the Related Art

Tumors/cancers have always been a threat to the health of human beings. For many years, the medicinal field has endeavored to research and develop effective medicines for the treatment of tumors/cancers. However, up to the present, there is not any medicine that is effective in the clinical treatment of tumors/cancers, particularly in the treatment of liver tumor-related diseases (such as hepatocellular carcinoma).

At present, the cell therapy for metastasized liver cancer or liver cancer that has undergone unsuccessful localized treatment is mainly performing a transcatheteral arterial embolization (TAE) or a percutaneous ethanol injection, or adopting a systemic chemotherapy, such as administration of doxorubicin, a combination of tamoxifen in high dose and doxorubicin, or combined chemotherapy (cisplatin+5-FU+ leucovorin, abbrev. PFL). Although the remission rate of these anti-cancer medicines can be up to 15~30%, since most of the liver cancer patients have liver cirrhosis and/or other complications (such as leukocyte reduction, platelet reduction, or liver function decompensation), systemic chemotherapy is not suitable for such patients. Therefore, chemotherapy is unable to effectively extend the overall survival of patients suffering from liver cancer. Since 1990, arseniccontaining compounds (arsenicals) have provided another direction for research and development in the treatment of tumors/cancers.

It was reported that when arsenic trioxide was administered intravenously at a dose of 10 mg/d to patients with relapsed acute promyelocytic leukemia, a complete remission (CR) rate of 90% could be achieved. (See Shen Z. X. et al., *Blood* (1997), 89: 3354). It was also reported that, other than arsenic trioxide, arsenic-containing substances such as "Composite Indigo Naturalis Tablets" containing arsenic sulfide ($As_2S_2$) and pure tetraarsenic tetraslfide ($As_4S_4$) can achieve complete remission rates of 98% and 84.9%, respectively. (See Wang Z. Y., *Cancer Chemother Pharmacol* (2001), 48 (suppl 1): S72-S76).

Clinical studies further indicated that low-dose arsenic trioxide administered intravenously to patients with relapsed acute promyelocytic leukemia at a daily dose of 0.08 mg/kg for 28 days could achieve a complete remission rate of 80%, and that side effects caused by arsenic trioxide (such as gastrointestinal disturbance, facial edema and cardiac toxicity) were reduced. (See Shen Y, et al., *Leukemia* (2001), 15: 735-741).

It was also reported that for patients with relapsed acute promyelocytic leukemia or all-trans-retinoic acid (ATRA) resistant acute promyelocytic leukemia, the administration of a combination of arsenic trioxide and other drugs (such as GM-CSF) resulted in a synergistic therapeutic effect. (See Muto A et al., *Leukemia* (2001), 15(8): 1176-1184).

In recent years, the medical field has gradually explored the mechanism of arsenic trioxide in the treatment of acute promyelocytic leukemia. According to reports, the mechanism of arsenic trioxide in inhibiting acute promyelocytic leukemia cell lines may be the triggering of apoptosis at relatively high concentrations (from 0.5 to 2 µmol/L) and the induction of cell differentiation at low concentrations (from 0.1 to 0.5 µmol/L). (See Chen G Q, et al., *Blood* (1997), 89: 3345).

In 2002, Miller et al., propounding the possible mechanisms of actions of arsenic trioxide in *Cancer Research* (2002), 62:3893-3903, stated that these actions might result in the induction of apoptosis, the inhibition of growth and angiogenesis, and the promotion of differentiation, and that because arsenic affected so many cellular and physiological pathways, a wide variety of malignancies, including both hematologic cancer and solid tumors derived from several tissue types, might be susceptible to therapy with arsenic trioxide.

In 2001, the National Institutes of Health (NIH) of the United States proceeded with clinical trials of arsenic trioxide in hematologic and solid tumors, and indicated in their reports that arsenic trioxide can inhibit growth of many cancer cell lines, and promote apoptosis in the cancer cell lines. The clinical trials of arsenic trioxide conducted in connection with hematologic malignancies include, in addition to acute promyelocytic leukemia, acute myeloid leukemia (AML), acute lymphocytic leukemia, chronic myelogenous leukemia (CML), non-Hodgkin's lymphoma, Hodgkin's lymphoma, chronic lymphocytic leukemia, myelodysplastic syndrome and multiple myeloma. The clinical trials of arsenic trioxide conducted in connection with solid tumors include prostate cancer, cervical cancer and bladder cancer. (See Murgo A. J., *The Oncologist* (2001), 6 (suppl 2):22-28).

In September 2000, the Food and Drug Administration (FDA) of the United States approved arsenic trioxide as an orphan drug for treating acute promyelocytic leukemia. The Department of Health (DOH) of Taiwan, R.O.C., approved marketing of an arsenic trioxide-containing pharmaceutical preparation ("ASADIN Injection"; license no. 000005) by TTY Biopharm Co., Ltd. (Taiwan), in January, 2002.

In recent years, studies on the treatment of solid tumors with arsenic trioxide have gradually developed in China. It was indicated in a report that in an evaluation of the therapeutic efficacy of arsenic trioxide using an animal model of mice with liver tumor, the result showed that the life of the mice could be extended to 127.2% after administration of arsenic trioxide at a dose of 2 mg/kg for 10 consecutive days. (See Lin et al., "Study on Anti-tumor Activity of Arsenic Trioxide," China Journal of Chinese Materia Medica (1999), 24(3): 1-3).

WO 99/24029 (corresponding to CN 1285743A) discloses methods for the treatment of leukemia, lymphoma, and solid tumors, which includes administering to a patient a therapeutically effective amount of arsenic trioxide or an organic arsenical, i.e. melarsoprol, which can be used in combination with other therapeutic agents (such as chemotherapeutics, radioprotectants, radiotherapeutics or other medical techniques so as to improve the quality of life of the patient. In addition, the pharmaceutical composition used in the aforesaid patent is a substantially sterile solution suitable for intravenous injection or infusion, and is also suitable for oral delivery, or topical or transdermal delivery. The preparation of the sterile solution involves the adjustment of specific pH values.

In the treatment of tumors/cancers, in addition to chemotherapeutics, radiation has been used by the medical field in the diagnosis and treatment of diseases, particularly in the treatment of cancers (such as skin cancers and nasopharyngeal cancers) since the discovery of the radioactive Ra element ($^{226}$Ra) by the Curies in 1898. With the development in the research of the radionuclide science after World War II, scientists have gained a better understanding of the effects of radiation on living creatures, which has further improved methods and techniques of radiation therapy, increased the rate of survival, and prolonged lifespan, while reducing the side effects of radiation on normal tissues.

Internal radionuclide therapy (IRT) works by the principle of delivering large radiation doses to the targeted diseased tissues by using appropriate radiopharmaceuticals (RPs) while sparing normal tissues. For selective localization, either ions or molecules that are specific to diseased tissues are used as carriers for therapeutic radionuclides or soluble and microparticulate radiopharmaceuticals (RPs) are introduced regionally to increase uptake or to confine the RP in a body cavity.

Radionuclides for therapeutic use should be able to emit radiations that have high linear energy transfer (LET) in order to destroy malignant and other rapidly proliferating cell populations. They include (1) β emitting radionuclides, (2) α emitting radionuclides and (3) radionuclides that decay by electron capture (EC) and internal conversion (IC) to result in the emission of Auger and Coster-Kronig (C-K) electrons. The range of β particles is in mm's so that they are effective for large tumors. The range of α particles is 50-100 μm so that they are effective for small tumors and micrometastases. Radionuclides that emit Auger and C-K electrons are effective only when they are carried across the cell membrane into the nucleus to damage DNA, because the range of these electrons is <0.1 μm.

The aforesaid is based on the review article by Meral Tayan Ercan and Meltem Caglar in *Current Pharmaceutical Design* (2000), 6:1085-1121. Various radionuclides are listed in tables 1 and 2 of said review article, including $^{32}$P, $^{67}$Cu, $^{76}$As, $^{89}$Sr, $^{90}$Y, $^{131}$I, $^{153}$Sm, $^{165}$Dy, $^{166}$Ho, $^{169}$Er, $^{186}$Re, $^{188}$Re, $^{198}$Au, $^{211}$At, $^{212}$Bi and $^{213}$Bi, of which $^{131}$I is the most widely used therapeutic radiopharmaceutical and is used for the treatment of thyroid cancer and hyperthyroidism. Table 3 of said review article also mentioned several radionuclides, which are prepared in specific forms of therapeutic radiopharmaceuticals for particular applications. However, said review article is silent on the preparation of therapeutic radiopharmaceuticals from arsenic-containing compounds, such as arsenic trioxide, arsenic trisulfide and arsenic sulfide.

In 2002, Yong-Jin Chun et al., described in *FEBS Letter*, (2002), 519: 195-200, that arsenic trioxide can sensitize human cervical cancer cells to ionizing radiation both in vitro and in vivo, and that the combined treatment of arsenic trioxide in chemotherapy and ionizing radiation has a synergistic effect in the treatment of cervical cancer.

All literatures and patents mentioned hereinabove, as well as the literatures cited therein, are incorporated herein by reference in their entirety.

SUMMARY OF THE INVENTION

For developing an effective drug for the treatment of tumors/cancers, the Applicants attempt to combine chemopharmaceutical therapy and radiation therapy, and provide a process for preparing a radioactive arsenic-containing compound, the process includes the steps of:
  (i) subjecting an arsenic-containing compound selected from a group consisting of $As_2O_3$, $As_2S_3$, $As_2S_2$, and a combination thereof to a neutron irradiation treatment such that the arsenic element contained in the arsenic-containing compound is converted to a radioactive arsenic isotope; and
  (ii) recovering the resultant product from step (i)

This invention also provides a pharmaceutical composition, which includes:
  (a) a therapeutically effective amount of a radioactive arsenic-containing compound, the radioactive arsenic-containing compound being prepared by a process comprising the steps of:
    (i) subjecting an arsenic-containing compound selected from the group consisting of $As_2O_3$, $As_2S_3$, $As_2S_2$, and a combination thereof to a neutron irradiation treatment such that the arsenic element contained in the arsenic-containing compound is converted to a radioactive arsenic isotope; and
    (ii) recovering the resultant product from step (i); and
  (b) a pharmaceutically acceptable carrier.

The pharmaceutical composition according to this invention can be used in the treatment of tumors/cancers, such as hematological malignancies and solid tumors, and has a more significant therapeutic effect compared to that of the existing arsenic trioxide-based anti-cancer drugs (such as those disclosed in the aforesaid patents or literatures).

BRIEF DESCRIPTION OF THE DRAWINGS

Other features and advantages of the present invention will become apparent in the following detailed description of the preferred embodiment(s) of the invention, with reference to the accompanying drawings, in which.

DETAILED DESCRIPTION OF THE PREFERRED EMBODIMENT(S)

Figure 1:
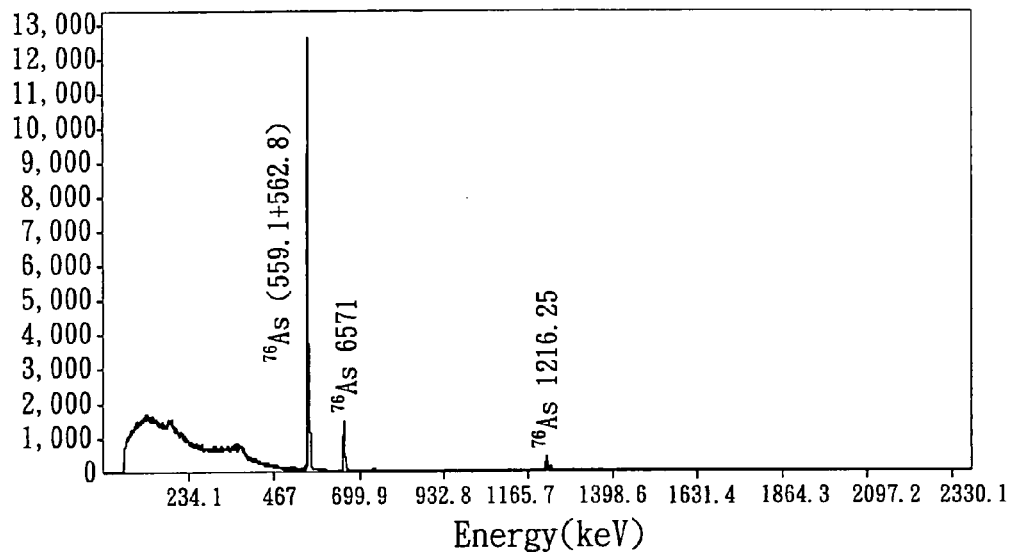
FIG. 1 shows the gamma-energy spectrum of the arsenic element $^{75}As(n,\gamma)^{76}As$ contained in arsenic trioxide after neutron irradiation treatment.

The present invention provides a pharmaceutical composition, which includes:
  (a) a therapeutically effective amount of a radioactive arsenic-containing compound, the radioactive arsenic-containing compound being prepared by a process comprising the steps of:

(i) subjecting an arsenic-containing compound selected from the group consisting of $As_2O_3$, $As_2S_3$, $As_2S_2$, and a combination thereof to a neutron irradiation treatment such that the arsenic element contained in the arsenic-containing compound is converted to a radioactive arsenic isotope; and (ii) recovering the resultant product from step (i); and (b) a pharmaceutically acceptable carrier.

The present invention also provides a process for preparing a radioactive arsenic-containing compounds, which includes the steps of:

(i) subjecting an arsenic-containing compound selected from a group consisting of $As_2O_3$, $As_2S_3$, $As_2S_2$, and a combination thereof to a neutron irradiation treatment such that the arsenic element contained in the arsenic-containing compound is converted to a radioactive arsenic isotope; and (ii) recovering the resultant product from step (i).

The neutron irradiation treatment used in the process of this invention is known to one skilled in the art (see, for example, Samir C. Mehta and D. Robert Lu (1996), *Pharmaceutical Research*, 13 (3): 344-351). In this invention, a selected arsenic-containing compound can be placed in an atomic reactor and the arsenic-containing compound can then be subjected to neutron irradiation treatment for initiating a nuclear reaction so as to convert the arsenic element contained in the arsenic-containing compound.

In a preferred embodiment of this invention, the arsenic-containing compound used in the neutron irradiation treatment is $As_2O_3$.

In another preferred embodiment of this invention, the radioactive arsenic-containing compound produced by the process of this invention can emit γ particles and β particles.

In still another preferred embodiment of this invention, the radioactive arsenic-containing compound produced by the process of this invention contains $^{76}As$ isotope.

In a further preferred embodiment of this invention, the radioactive arsenic-containing compound produced by the process of this invention is radioactive arsenic trioxide, which can emit γ energy [0.559 MeV (45%), 0.563MeV (1.2%), 0.657MeV (6.2%)] and β energy [1.75MeV (8%), 2.40 MeV (35%), 2.96 MeV (51%)]. The half life of $^{76}As$ ($T_{1/2}$) is 26.5 hours.

The radioactive arsenic-containing compound according to this invention has been tested and demonstrated to have an activity of inhibiting the growth of tumor cells. Therefore, it is contemplated by this invention that the radioactive arsenic-containing compound is useful in the manufacture of pharmaceutical compositions.

Accordingly, this invention also provides a pharmaceutical composition, comprising:

(a) a therapeutically effective amount of a radioactive arsenic-containing compound prepared by the aforesaid process; and (b) a pharmaceutically acceptable carrier.

According to this invention, the pharmaceutical composition can be used in the treatment of a tumor or cancer. Preferably, the tumor or cancer is selected from a group consisting of hematological malignancies and solid tumors.

Preferably, the solid tumor is selected from a group consisting of breast cancer, rectal cancer, liver tumor, ovarian cancer and prostate cancer. More preferably, the solid tumor is selected from a group consisting of hepatocellular carcinoma, cholangiocarcinoma, liver cell carcinoma, fibrolamellar variant of hepatocellular carcinoma, intrahepatic bile duct carcinoma, mixed hepatocelluar cholangicocarinomoa, undifferentiated hepatocellular carcinoma, hepatoma with tumor invasion to common bile duct, hepatoblastoma, childhood hepatic tumor, and primary hepatocellular carcinoma.

Preferably, the hematological malignancy is leukemia or lymphoma. More preferably, the hematological malignancy is selected from a group consisting of acute promyelocytic leukemia (APL), acute myeloid leukemia(AML), acute lymphocytic leukemia, chronic myeloid leukemia (CML), non-Hodgkin's lymphoma, Hodgkin's lymphoma, chronic lymphocytic leukemia, myelodysplastic syndrome and multiple myeloma.

According to this invention, the term "therapeutically effective amount" as used herein means an amount of a radioactive material-containing pharmaceutical composition which is sufficient to achieve the intended therapeutic effect without causing undesired serious radiation damage to non-targeted tissues or organs when administered to a mammal in need of the composition for treatment. The therapeutically effective amount will vary depending on different factors. These factors include, for instance, the type of disease, the age, bodyweight, health condition and response of the subject to be treated, and the route of administration, etc. The therapeutically effective amount can be determined by one skilled in the art.

The pharmaceutical composition of this invention can be formulated by techniques which are well known to one skill in the art into forms suitable for parenteral, oral, or topical administration, such as solution, capsule, dispersion, suspension, and so on.

Preferably, the pharmaceutical composition according to this invention is formulated into forms suitable for injection, such as powder injection, lyophilization product for injection, emulsion injection, oily injection, liposome injection, etc.

According to this invention, the term "pharmaceutically acceptable carrier" as used herein means any carrier known in the art to be suitable for the manufacture of pharmaceuticals and including, but not limited to, water, normal saline, glycerol, organic solvents, stabilizers, chelating agents, preservatives, emulsifiers, suspending agents, diluents, gelatinizers, and liposomes.

The dosage and administration frequency of the pharmaceutical composition according to this invention will vary depending on the following factors: the severity of the disease to be treated, the administration route, and the body weight, age, health condition and response of the subject to be treated. Generally, the pharmaceutical composition according to this invention is administered parenterally, orally, or topically in an amount of 0.01 to 0.6 mg/Kg of body weight per day, in single or multiple doses. Preferably, the pharmaceutical composition of this invention is administered by continuous intravenous injection, topical arterial single injection and topical tumor direct injection.

The pharmaceutical composition of this invention can be administered daily for a period of up to 60 days or until remission, followed by 2 to 10 more courses, each lasting 5 to 60 days.

In a preferred embodiment of this invention, the radioactive arsenic-containing compound is neutron-irradiated arsenic trioxide, and is formulated into an aqueous injection formulation. In a more preferred embodiment, the aqueous injection formulation includes an appropriate amount of the radioactive arsenic trioxide, ethylene diamine tetracetic acid disodium salt, a buffer, and water.

In a more preferred embodiment, the aqueous injection formulation has a radioactivity in a range of from 2 to 4 mCi/ml. In a more preferred embodiment, the aqueous injection formulation has a radioactivity in a range of from 2.77 to 3.25 mCi/ml.

In a preferred embodiment, for a patient with liver cancer, the pharmaceutical composition according to this invention can be administered by means of hepatic artery single injection and liver tumor direct injection. Liver tumor direct injection is more preferred.

The pharmaceutical composition according to this invention can be administered singly or in combination with other medicines or therapeutic methods for treating tumors/cancers. Such other medicines include, but are not limited to, doxorubicin, tamoxifen, taxol, nitrogen mustard, 5-flurouracil, vinblastine and all-trans-retinoic acid. The therapeutic methods include chemotherapy and external beam radiation therapy.

This invention will be further explained by way of the following Examples. It is understood that the following Examples are illustrative of the invention, but are not to be construed as limiting the scope of the invention.

EXAMPLES

1. Animal Source:

Male Spawn-Dawley rats (5-week-old, 150 g) purchased from the animal center of National Yang-Ming University, Taiwan (R.O.C.) and the animal center of National Science Council, Taiwan (R.O.C.), respectively, were used in the following experiments. After purchase, the rats were kept at the animal room of the Institute of Nuclear Energy Research, Atomic Energy Council, Administrative Yuan, Taiwan (R.O.C.), under constant conditions of temperature, moisture, and photoperiodism. During the period of rearing, water and feed were not limited, and bedding was regularly replaced twice a week.

into an aluminum capsule so as to act as an irradiation target during irradiation, and a neutron irradiation treatment was performed for a period of 30 hours under operational conditions that would enable the resultant product to have a radioactivity of from 2 to 4 mCi.

After irradiation, the quartz tube was cut by a cutting tool, and 3 ml of 1N NaOH solution was added into the cut quartz tube to dissolve $As_2O_3$. 1 ml of 1N HCl solution was added thereto 20 minutes later. Finally, 1 ml of normal saline was added to adjust the concentration of the solution to 1 mg/ml. Gamma-energy spectrum analysis of the irradiated arsenic trioxide-containing solution thus obtained was conducted using Multi-channel Analyzer (MCA).

Non-irradiated arsenic trioxide was formulated in the same fashion into a solution with a concentration of 1 mg/ml for use as a control in the following animal experiments.

Results:

FIG. 1 shows the result of the gamma-energy spectrum analysis of the neutron-irradiated arsenic trioxide-containing solution. In addition, Table 1 below shows the nuclear data of the arsenic element included in the neutron-irradiated arsenic trioxide. As shown by the results of this Example, nuclear reaction was initiated when arsenic trioxide was subjected to the neutron irradiation in the atomic reactor, thereby producing a radioactive nucleus, which emits not only gamma energy [0.559 MeV (45%), 0.563 MeV (1.2%), 0.657 MeV (6.2%)] but also beta energy [1.75 MeV (8%), 2.40 MeV (35%), 2.96 MeV (51%)]. Therefore, neutron-irradiated arsenic trioxide can be used in the treatment of tumors/cancers (for killing cancer cells).

TABLE 1

Nuclear energy data of the arsenic element in neutron-irradiated arsenic trioxide

| Element | Target Nuclei | Natural existence (%) | Nuclear Reaction | a. synthesis | Half-life | Thermal neutron cross section $\sigma_{th}(b)$ | Gamma energy Emitted (MeV) | Beta energy emitted (MeV) |
|---|---|---|---|---|---|---|---|---|
| As | $^{75}As$ | 100 | (n, γ) | $^{76}As$ | 26.5 hrs | 4.4 | 0.559-45% <br> 0.563-1.2% <br> 0.657-6.2% <br> 1.213-1.4% | 1.75-8% <br> 2.40-35% <br> 2.96-51% |

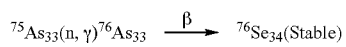

$^{75}As_{33}(n, \gamma)^{76}As_{33} \xrightarrow{\beta} {}^{76}Se_{34}(Stable)$ 2. Source of Tumor Cell:

The tumor cells for the establishment of the animal model with liver tumors were N1-S1 rat hepatoma cells purchased from the American Type Culture Collection (ATCC, P.O. Box 1549, Manassas, Va. 20108 USA). The rat hepatoma cells N1-S1 were subjected to successive sub-cultures to set up a Master Cell Bank and a Working Cell Bank.

Example 1

Preparation of Radioactive Arsenic Trioxide 5 mg of arsenic trioxide powder (available from TTY Biopharm Co., Ltd.) was added to a quartz tube (Quartz® glass, Toshiba, Japan), and the opening of the quartz tube was completely sealed by a mixed flame of gas/oxygen. The quartz tube was wrapped with aluminum foil and then placed Example 2

Establishment of an Animal Model with Liver Tumor

Operational Method:

The tumor cells for the establishment of the animal model with liver tumor were of a rat hepatoma cell line, N1-S-1, purchased from the American Type Culture Collection (ATCC, P.O. Box 1549, Manassas, Va. 20108 USA), and were subcultured to set up a Master Cell Bank and a Working Cell Bank.

The rat hepatoma cells, N1-S1, were suspended cells that were dispersed in Iscove's Modified Dulbecco's Medium (IMDM) (GibcoBRL®) supplemented with 1% penicillin (GibcoBRL®) and 10% fetal bovine serum (GibcoBRL®), and were cultured in an incubator with 5% $CO_2$, at 37° C.

When cultured to $1.5 \times 10^6$ cell/ml, $4 \times 10^6$ cell/0.06 ml of N1-S1 cells were sampled and then implanted into Spawn-Dawley male rats (5-week-old, 150 g) between the liver and liver capsule by surgery, and the wounds were closed by sutures. Rearing of the rats was continued for ten days, and ultrasonic scanning was used to detect any growth of liver tumor and tumor size. After scanning, animals that had developed liver tumors were used to conduct the experiments of tumor growth inhibition, and euthanasia was practiced on the rest of the rats.

Result:

N1-S1 rat hepatoma cells subcultured for 2, 7 and 9 passages were used to establish the animal model with liver tumors. The results of comparison are shown in Table 2.

TABLE 2

The tumor incidence for rats implanted with N1-S1 rat hepatoma cells of different passages.

| Number of passages | Date of tumor implantation (m/d/y) | Number of implanted animals | Date of test being conducted (m/d/y) | Number of animals with developed tumor | Tumor incidence |
| --- | --- | --- | --- | --- | --- |
| 9 | 07 17, 02 | 70 | 07 31, 02 | 20 | 28.57% |
| 7 | 08 07, 02 | 70 | 08 21, 02 | 25 | 35.71% |
| 7 | 08 14, 02 | 70 | 08 28, 02 | 26 | 37.14% |
| 2 | 10 07, 02 | 40 | 10 31, 02 | 25 | 62.5% |
| 2 | 11 11, 02 | 50 | 11 21, 02 | 30 | 80% |

10 days after the N1-S1 rat hepatoma cells subcultured for 9 passages were implanted into the livers of the 5-week-old rats, the incidence of liver tumor in the rats was about 30%. 10 days after the N1-S1 rat hepatoma cells subcultured for 7 passages were implanted into the livers of the 5-week-old rats, the incidence of liver tumor in the rats was about 35%. 10 days after the N1-S1 rat hepatoma cells subcultured for 2 passages were implanted into the livers of the 5-week-old rats, the incidence of liver tumor in the rats was about 70%.

At the initial stage of this experiment, use of the hepatoma cell line subcultured for 9 passages resulted in a liver tumor incidence of about 30% and unsatisfactory tumor growth condition. When cells subcultured for 2 passages were instead implanted into the bodies of the rats, the liver tumor growth incidence was raised to 70%, and the growth condition was better. Therefore, it was found in the experiment that, 10 days after the N1-S1 hepatoma cell line was implanted into the bodies of the rats, not all of the rats would develop liver tumors, and the incidence of liver tumor growth was relatively low. After development of liver tumor, the tumor might, due to self-elimination in the rats, shrink or even disappear without any medical treatment.

Accordingly, it is determined that in a cell line with a low passage number, the cells have not yet experienced any morphological change, and the condition thereof is better and more stable so that the incidence of inducing liver tumor in the rats is considerably increased. In addition, when a cell line with a low passage number is used, if the rats are not given medication after development of liver tumors, the liver tumors in the rats will continue growing and finally result in the death of the rats due to metastasis and ascites.

The liver tumor animal model established using rats in this experiment is a stable animal model. However, in the selection of cell lines, it is preferred to use a cell line of less than 5 passages so as to maintain the growth condition of the tumor cell line.

Example 3

Biodistribution Test

Hepatic Artery Injection:

The hepatic artery was dissected from the hepatic tissue of the rats by surgery. A PE-10 tube was introduced into the hepatic artery, and the test solution containing neutron-irradiated arsenic trioxide as prepared in Example 1 was injected into the hepatic artery. The PE-10 tube was removed after injection, and a surgical thread was used to bind and fix the blood vessels, followed by suturing of the wound.

Tail Vein Injection:

The test injection solution containing neutron-irradiated arsenic trioxide as prepared in Example 1 was injected into the tail vein using a syringe with needle no. 25.

Operational Method:

A fixed amount of radioactive arsenic trioxide (radioactivity range: 2.77~3.25 mCi/ml, concentration: 1 mg/ml, animal injection dose: 0.45 mg/kg) prepared in Example 1 was injected into the rats with liver tumors through the hepatic artery and tail vein, respectively.

The rats were sacrificed by taking a large amount of blood from the heart at hours 2, 4, 16, 24 and 48, respectively, after injection, and the blood, hearts, lungs, livers, spleens, kidneys, intestines, bladders, muscles, and tumors were removed. These tissues or organs were placed in respective tubes, and their irradiation intensity was measured by a gamma counter (Wallac 1470 WIZARD). The content percentage of arsenic trioxide per each gram of the tissue or organ was calculated using standard curve regression. There were two or three experimented rats in each experimental group.

Some of the organs and tissues (blood, kidneys and livers) were transferred to the Institute of Nuclear Energy Research for conducting Inductively Coupled Plasma Mass Spectrometry (ICP-MAS) so as to observe the biodistribution of arsenic trioxide in the tumors and organs or tissues.

Result:

The therapeutic effect and metabolic pathway of arsenic trioxide in the treatment of various malignant tumors in humans have been widely studied and discussed; however, the biodistribution thereof within living creatures is still not clear.

Figure 2:
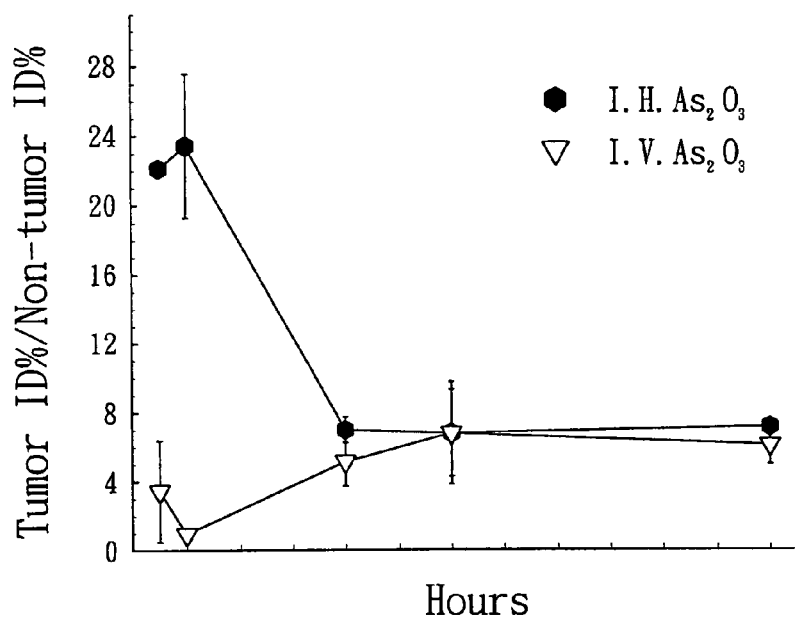
FIG. 2 shows the distribution of the radioactive arsenic trioxide according to this invention in the tumors in the rats at different times after tail vein injection and hepatic artery injection.
Figure 3:
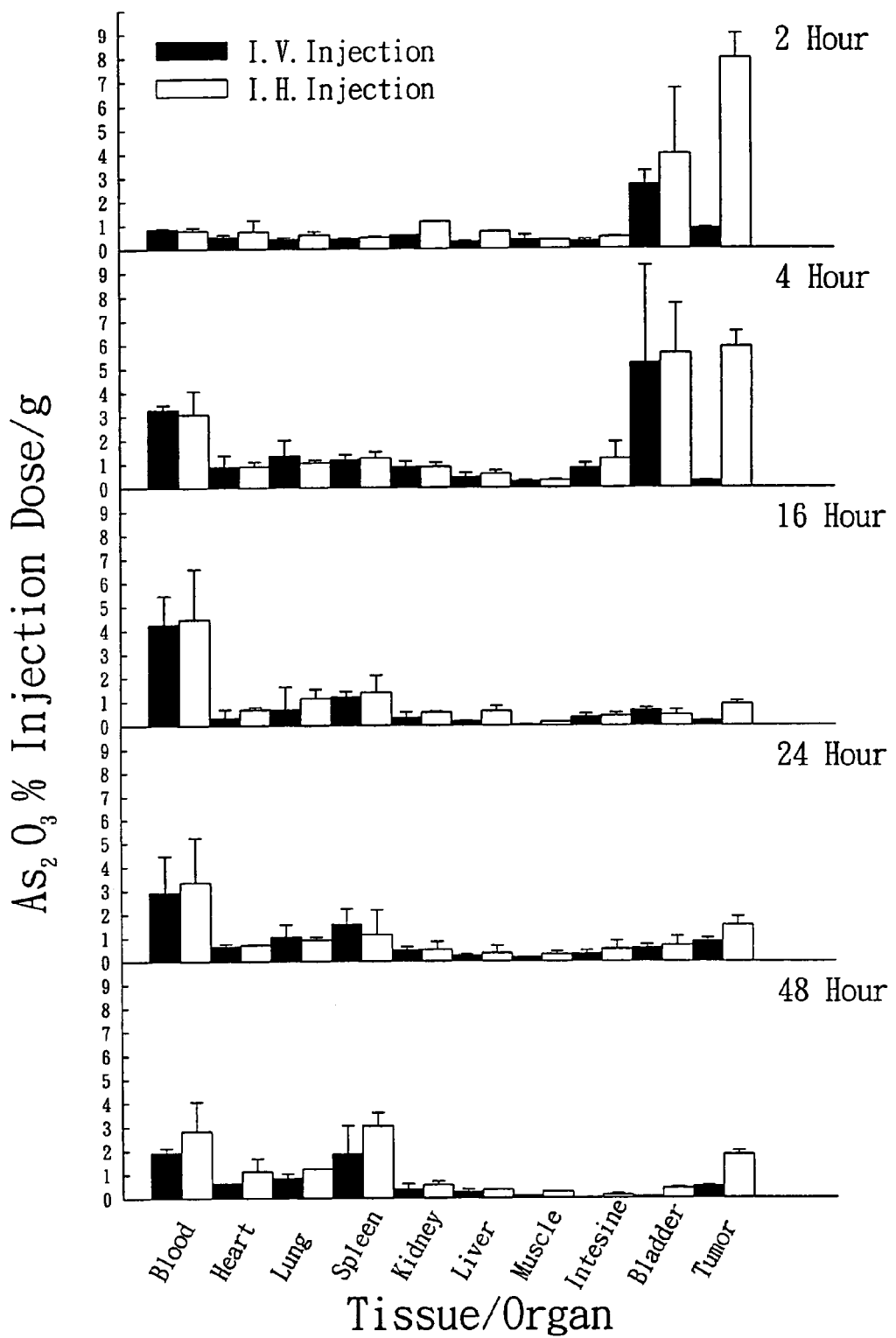
FIG. 3 shows the distribution of the radioactive arsenic trioxide according to this invention in the tissues or organs of the rats at different times after tail vein injection and hepatic artery injection.

This experiment illustrates the biodistribution of radioactive arsenic trioxide in the tumors and each of the organs as observed at hours 2, 4, 16, 24, and 48, respectively, after injection of the radioactive arsenic trioxide into the rats through the hepatic artery and tail vein. FIG. 2 shows the biodistribution of the radioactive arsenic trioxide according to this invention in the tumors in the rates at different times after injection through the hepatic artery and tail vein. FIG. 3 shows the biodistribution of the radioactive arsenic trioxide according to this invention in each of the organs of the rats at different times after injection through the hepatic artery and tail vein.

Radioactive arsenic trioxide was injected respectively into the tail vein and hepatic artery of the rats by I.V. and I.H. The dosage was calculated using MIRD method, and the residence time in each of the organs and the tumors was calculated using Excel software. Finally, the radiation absorption dose in each of the organs or tissues and the tumors was calculated using MIROSE 3 software. The results are shown in Table 3 below.

TABLE 3

Radiation absorption dose in each of the organs or tissues and the tumors after injection of radioactive arsenic trioxide into the animals through the tail vein and hepatic artery, respectively, by I.V. and I.H.

|  | IV (mGy/MBq) | IH (mGy/MBq) |
| --- | --- | --- |
| Lung | 0.47 | 0.56 |
| Spleen | 0.76 | 0.95 |
| Kidney | 0.25 | 0.28 |
| Liver | 0.13 | 0.21 |
| Muscle | 0.06 | 0.12 |
| Intestine | 0.16 | 0.23 |
| Tumor | 4.26 | 21 |

The radiation absorption doses in the tumors after injection of radioactive arsenic trioxide via the hepatic artery and the tail vein were 21 mGy/MBq and 4.26 mGy/MBq, respectively, the difference therebetween being as large as 5 times, whereas those in the other organs, including lungs, spleen, kidney, and liver, appeared to be similar.

After injection of the radioactive arsenic trioxide via the hepatic artery, the content of the radioactive arsenic trioxide in the liver tumor reached its peak during the interval between hours 2 and 4, and was obviously higher than the result obtained in the experimental group which had tail vein injection. In the experimental group with hepatic artery injection, 4 hours after injection, the content of the radioactive arsenic trioxide in the liver tumor went down to achieve balance. In the experimental group adopting tail vein injection, the content of the radioactive arsenic trioxide in the liver tumor had the tendency to go up gradually 4 hours after injection. In the two experimental groups which adopted different routes of administration, the contents of the radioactive arsenic trioxide in the liver tumors reached identical equivalent values 16 hours later (FIG. 2).

The contents of arsenic trioxide in the blood, kidney, and liver were analyzed by ICP-MAS, and the obtained results (not shown) tend to be identical to those of the biodistribution test using radiation analysis.

Of the tested organs, the contents of radioactive arsenic trioxide in the bladder and urine were second only to that in the tumor at hour 4 after injection via the hepatic artery and tail vein. The contents of the radioactive arsenic trioxide in the heart, the lung, and the spleen were all maintained within a certain range (1~3% ID/g.) (FIG. 3).

Furthermore, the residual contents of the radioactive arsenic trioxide in all the organs or tissues dropped 48 hours after injection (FIG. 3), and the results of administration through IV and IH (FUG. 2) were very close. These results should be able to support that the pharmaceutical composition containing radioactive arsenic trioxide is suitable for systemic administration.

Additionally, this experiment indicated that, regardless of the method of injection, the extent of accumulation of arsenic trioxide in the tumor is a fixed value, and that, no matter which injection method is employed, there is a certain extent of accumulation of arsenic trioxide in the heart, lung, and spleen. Both arsenic trioxide and radiation might cause damage to such tissues and organs; therefore, the radioactive arsenic trioxide of this invention can be formulated in a suitable carrier so that it can be retained within the liver tumor more specifically while causing no harm or less harm to nearby tissues and organs.

Example 4

Therapeutic Effect Assessment

A. Continuous Vein Injection

The rats with liver tumors were given normal saline, an injection solution containing arsenic trioxide without neutron irradiation treatment (concentration: 1 mg/ml; animal injection dosage: 0.45 mg/kg), and the injection solution prepared in Example 1 which contained radioactive arsenic trioxide having subjected to neutron irradiation treatment (radioactivity range: 2.77~3.25 mCi/ml; concentration: 1 mg/ml; and animal injection dosage: 0.45 mg/kg), respectively, via tail vein injection, and the injection was continued for two weeks.

Before injection, the size of the liver tumors was examined by ultrasonic scanning. Ultrasonic scanning was conducted in the first week, the second week, and the fifth week, respectively, after start of the injection so as to observe the change in size of the tumor. Finally, the rats were sacrificed for observing whether there was metastasis.

B. Hepatic Artery Single Injection

The blood vessels of the hepatic artery were dissected from the hepatic tissue of the rats by surgery, and normal saline, an injection solution containing arsenic trioxide without neutron irradiation treatment (concentration: 1 mg/ml; and animal injection dosage: 0.45 mg/kg), and the injection solution prepared in Example 1 which contained radioactive arsenic trioxide having subjected to neutron irradiation treatment (radioactivity range: 2.77~3.25 mCi/ml; concentration: 1 mg/ml; and animal injection dosage: 0.45 mg/kg dose), were injected respectively via the hepatic artery in single injections.

Before injection, the size of the liver tumors was examined by ultrasonic scanning. Ultrasonic scanning was conducted in the first week, the second week, and the fifth week, respectively, after start of the injection to observe the change in size of the tumor. Finally, the rats were sacrificed for observing whether there was metastasis.

C. Liver Tumor Direct Injection

The rats with liver tumors were subjected to surgery. After the locations of the liver tumors were found, the tumors were directly injected with normal saline, an injection containing arsenic trioxide without neutron irradiation treatment (concentration: 1 mg/ml; animal injection dosage: 0.45 mg/kg), and the injection prepared in Example 1 which contained radioactive arsenic trioxide having subjected to neutron irradiation treatment (radiation activity range: 2.77~3.25 mCi/ml; concentration: 1 mg/ml of concentration; and animal injection dosage: 0.45 mg/kg), respectively, once every week, twice in total.

Before injection, the size of the liver tumors was examined by ultrasonic scanning. Ultrasonic scanning was conducted in the first week, the second week, and the fifth week, respectively, after start of the injection to observe the change in size of the tumor. Finally, the rats were sacrificed for observing whether there was metastasis.

Results:

A. Continuous Vein Injection

Table 4 below shows the experimental results of continuous vein injection.

after injection, and all the tumors were found to have enlarged. The tumors had the tendency to shrink in week 1. In week 5, the tumors did not show much change. Rats that did not die of anesthesia were still alive in week 8.

In the rats that were given neutron-irradiated arsenic trioxide via tail vein injection, the tumors showed signs of growth 1 week after injection, but had the tendency to shrink in week 2. When measurement was taken in week 5, although the size of the tumors was bigger than when in week 1, it was smaller than that when examined 2 weeks after injection. The rats in this group were all alive in week 8.

In the experimental group injected with normal saline, although the tumors in some of the rats appeared to shrink slightly two weeks after injection, their life spans were shorter than those in the groups subjected to arsenic trioxide

TABLE 4

Size of liver tumors and survival time of the rats after being given normal saline, arsenic trioxide, and radioactive arsenic trioxide by continuous tail vein injection

| No. | Before injection | Tumor Size (cm × cm) After injection | | | Increase (In) or Decrease (de) % | Response | Survival time (day) |
|---|---|---|---|---|---|---|---|
| | | Week 1 | Week 2 | Week 5 | | | |
| Normal saline group | | | | | | | |
| 254 | 1.38 × 0.921 | 1.61 × 1.13 | 0.989 × 0.391 | 1.85 × 1.47 | In 49.28% | Poor | 32 |
| 255 | 1.56 × 1.27 | 1.79 × 1.33 | 2.01 × 1.51 | 2.99 × 2.63 | In 230% | Poor | 37 |
| 258 | 1.59 × 1.20 | 2.1 × 1.95 | — | — | In 114% | Poor | 8 |
| 262 | 0.971 × 0.656 | 0.802 × 0.720 | 0.645 × 0.542 | — | In 142% | Poor | 28 |
| 273 | 1.42 × 1.08 | 1.14 × 1.01 | 2.5 × 2 | — | In 334% | Poor | 12 |
| Arsenic trioxide group | | | | | | | |
| 251 | 1.61 × 1.08 | 2.30 × 1.64 | — | — | In 116.93% | Poor | 14 |
| 253 | 1.32 × 0.97 | 2.03 × 1.41 | 1.71 × 1.40 | 1.28 × 0.933 | De 35.11% | Mild | 42 |
| 256 | 1.65 × 1.11 | 2.22 × 1.75 | — | — | In 12% | Poor | 7 |
| 268 | 1.249 × 0.976 | 2.04 × 1.46 | 1.54 × 1.23 | — | De 31.31% | Mild | 14 |
| 271 | 1.52 × 1.13 | 1.01 × 0.8 | 1.16 × 1.10 | 2.01 × 0.7 | In 14.13% | Poor | 40 |
| Radioactive arsenic trioxide group | | | | | | | |
| 252 | 1.21 × 0.92 | 2.06 × 1.53 | 1.73 × 1.44 | 1.49 × 1.24 | De 40.53% | Good | >56 |
| 259 | 1.68 × 1.18 | 2.32 × 1.46 | 1.90 × 1.45 | 1.08 × 0.78 | De 74.87% | Good | >56 |
| 260 | 1.26 × 1.01 | 2.16 × 1.62 | 1.89 × 1.79 | 1.67 × 1.49 | De 28.89% | Good | >56 |
| 265 | 1.20 × 0.834 | 1.96 × 1.48 | 1.42 × 0.954 | 0.906 × 0.556 | De 82.64% | Good | >56 |
| 274 | 1.84 × 0.815 | 0.998 × 0.684 | 0.943 × 0.516 | 0.919 × 0.304 | De 59.08% | Good | >56 |

Note:
Increase in size of tumor (In %) is classified as "Poor Response";
decrease in size of tumor within 0%-40% is classified as "Mild Response";
decrease in size of tumor to 50% or more or disappearance of tumor is classified as "Good Response."

The liver tumor-bearing rats that were given normal saline by tail vein injection began to die on day 8, and were found, by dissection, to have ascites. The size of the tumors was also found to be larger than that at the first ultrasonic scanning examination. The surviving rats were subjected to ultrasonic scanning five weeks after injection, and the size of the tumors was found to be also larger than that at the first ultrasonic scanning examination. The rats injected with normal saline were all dead 8 weeks after injection, and no metastasis was found after dissection.

The rats injected with non-irradiated arsenic trioxide via the tail vein were examined by ultrasonic scanning 1 week injection or radioactive arsenic trioxide injection. It was found by dissection that the tumors had grown deep into the hepatic tissues. Therefore, although the tumors appeared to shrink slightly when the planar size of the tumors was examined by ultrasonic scanning, the tumors actually had the tendency to grow, and resulted in death of the animals due to ascites. Therefore, their life spans were shorter than the groups treated with arsenic trioxide (anti-cancer medication) and the radioactive arsenic trioxide (radioactive medication) according to this invention.

In addition, in the experimental group treated with arsenic trioxide injection, some of the animals were dead in week 2 due to overdose of anesthesia. It was found by dissection that the tumors therein did not undergo metastasis or exhibit abnormality. Administration of arsenic trioxide to the surviving animals was continued. However, the effect of arsenic trioxide on the inhibition of tumor growth was not significant.

This experiment indicated that in the first week of a course of continuous tail vein injection, arsenic trioxide, as well as radioactive arsenic trioxide according to this invention, had yet to exhibit any effect on the inhibition of tumor growth, and the tumors in the bodies of the animals in all the groups had a tendency to grow. In the second week of the course of treatment, the medicines started to exhibit their inhibitory effect on the tumors, and the action of the radioactive arsenic trioxide according to this invention on the inhibition of the growth of tumors in the rats was most noticeable. It was determined from this result that the medicines did not produce any effect on the tumors during the first week of medical treatment, and that the medicines began to exert their growth inhibitory and remissive effects on the tumors in the second week of continued medication, but the tumors still did not disappear completely.

B. Hepatic Arterial Single Injection

Table 5 below shows the experimental results of using hepatic artery single injection.

After hepatic artery single injection of normal saline, arsenic trioxide, and radioactive arsenic trioxide according to this invention, in the experimental group receiving normal saline injections, the size of the liver tumors 5 weeks after injection was noticeably larger than the size of the liver tumors 1 week after injection, and there was death of the animals in 2 weeks after injection. In the experimental group receiving arsenic trioxide injections, the size of the tumors in some of the animals 5 weeks after injection was slightly smaller than the size of the tumors 1 week after injection, while the tumors in some of the animals still grew. In the experimental group injected with the radioactive arsenic trioxide of this invention, the tumors in some of the animals either shrank or disappeared 2 weeks after injection, and the tumors in the other animals disappeared and shrank 5 weeks after injection.

The therapeutic effect of single injections of arsenic trioxide directly through the hepatic artery was not satisfactory. Although the tumors in some of the animals appeared to shrink, the extent was not very large. However, hepatic artery single injection of radioactive arsenic trioxide according to this invention resulted in complete disappearance of the tumors in some of the animals 2 weeks after injection, and the tumors in the other animals also had the tendency to shrink

TABLE 5

Size of liver tumors and survival time of the rats after being given normal saline, arsenic trioxide, and radioactive arsenic trioxide by hepatic artery single injection

| | | Tumor Size (cm x cm) | | | | | |
|---|---|---|---|---|---|---|---|
| | Before | After injection | | | Increase (In) or | | Survival |
| No. | injection | Week 1 | Week 2 | Week 5 | Decrease (de) % | Response | time (day) |
| Normal saline group | | | | | | | |
| 502 | 1.29 x 0.764 | 1.52 x 0.875 | 1.31 x 1.05 | 2.35 x 1.01 | In 78.57% | Poor | 38 |
| 503 | 0.986 x 0.550 | 0.983 x 0.989 | 2.10 x 1.82 | 1.51 x 0.867 | In 36.07% | Poor | 36 |
| 506 | 0.729 x 0.642 | 0.823 x 0.733 | 1.26 x 1.15 | — | In 44.9% | Poor | 14 |
| 507 | 1.12 x 0.717 | 1.71 x 1.23 | 2.75 x 1.83 | 2.88 x 2.50 | In 242.31% | Poor | 38 |
| Arsenic trioxide group | | | | | | | |
| 512 | 1.40 x 0.900 | 2.07 x 1.60 | 1.85 x 1.28 | 1.90 x 1.60 | De 8.21% | Mild | >42 |
| 513 | 0.448 x 0.452 | 0.583 x 0.775 | 2.04 x 1.34 | 1.25 x 1.15 | In 218.15% | Poor | 36 |
| 523 | 1.10 x 0.867 | 1.22 x 0.856 | 1.17 x 1.14 | 2.86 x 2.37 | In 549.05% | Poor | 39 |
| 524 | 1.17 x 0.525 | 1.21 x 0.878 | 1.23 x 0.707 | 1.10 x 0.679 | De 29.69% | Mild | >42 |
| Radioactive arsenic trioxide group | | | | | | | |
| 515 | 0.940 x 0.414 | 1.71 x 0.775 | 2.29 x 1.51 | Disappeared | De 100% | Good | >42 |
| 518 | 0.683 x 0.539 | 0.25 x 0.989 | Disappeared | Disappeared | De 100% | Good | >42 |
| 519 | 0.875 x 0.600 | 1.27 x 1.07 | 1.79 x 1.09 | 0.972 x 0.819 | De 56.60% | Good | >42 |
| 521 | 0.783 x 0.598 | 0.878 x 0.625 | Disappeared | Disappeared | De 100% | Good | >42 |

Note:
Increase in size of tumor (In %) is classified as "Poor Response";
decrease in size of tumor within 0%-40% is classified as "Mild Response";
decrease in size of tumor to 50% or more or disappearance of tumor is classified as "Good Response."

immediately. It could be determined from this result that, when the animals were subjected to hepatic artery single injection with radioactive arsenic trioxide, the irradiation could destroy the liver tumor cells and tissues immediately.

C. Liver Tumor Direct Injection

Table 6 below shows the experimental results of employing liver tumor direct injection.

TABLE 6

Size of liver tumors and survival time of the rats after being given normal saline, arsenic trioxide, and radioactive arsenic trioxide by direct single injections through the liver tumor

| | Tumor size (cm × cm) | | | | | |
|---|---|---|---|---|---|---|
| | Before | After injection | | Increase(In) or | | Survival |
| No. | injection | Week 1 | Week 4 | Decrease (de)% | Response | time (day) |
| Normal saline group | | | | | | |
| 526 | 1.02 × 1.31 | 1.82 × 1.49 | 2.82 × 2.22 | In 144.13% | Poor | >30 |
| 528 | 2.07 × 1.55 | 2.71 × 2.07 | 3.03 × 2.77 | In 49.61% | Poor | >30 |
| 536 | 1.81 × 1.51 | 2.58 × 1.92 | 2.35 × 2.34 | In 11.01% | Poor | >30 |
| arsenic trioxide group | | | | | | |
| 525 | 1.23 × 1.03 | 2.24 × 1.40 | 1.90 × 1.50 | De 9.12% | Mild | >30 |
| 529 | 1.31 × 1.30 | 2.21 × 1.49 | 2.67 × 1.70 | In 37.84% | Poor | >30 |
| 533 | 1.12 × 1.08 | 1.50 × 1.87 | 1.21 × 1.19 | De 43.99% | Good | >30 |
| Radioactive arsenic trioxide group | | | | | | |
| 530 | 1.33 × 0.675 | 1.10 × 0.700 | 0.506 × 0.642 | De 57.81% | Good | >30 |
| 534 | 1.03 × 0.711 | 1.10 × 0.747 | 0.708 × 0.392 | De 66.22% | Good | >30 |
| 538 | 0.728 × 0.700 | 0.945 × 0.600 | 0.500 × 0.244 | De 78.48% | Good | >30 |

Note:
Increase in size of tumor (In %) is classified as "Poor Response";
decrease in size of tumor within 0%-40% is classified as "Mild Response";
decrease in size of tumor to 50% or more or disappearance of tumor is classified as "Good Response."

After direct injection of normal saline, arsenic trioxide, and radioactive arsenic trioxide according to this invention into the liver tumors, in the experimental group injected with normal saline, the size of the liver tumors 4 weeks after injection was noticeably larger than that of the liver tumors 1 week after injection. In the experimental group injected with arsenic trioxide, the size of the tumors in some of the animals 4 weeks after injection was slightly smaller than the size of the tumors 1 week after injection, while the tumors in some of the animals still grew. In the experimental group injected with the radioactive arsenic trioxide according to this invention, the tumors in all of the animals shrank in 4 weeks of injection. All of the animals were still alive at the date the project ended. It could hence be determined that when radioactive medicine was injected directly into the liver tumor, the irradiation could immediately destroy the liver tumor cells and tissues, and this result was similar to that in the case of single hepatic arterial injection of radioactive medication.

The three therapeutic effect assessments hereinabove can be summarized as follows:

I. Continuous intravenous injection with radioactive arsenic trioxide can inhibit the growth of liver tumors effectively, and can extend the survival time of animals with liver cancer; tail vein injection of non-radioactive arsenic trioxide has a comparatively small effect in the remission of liver tumors, but can also prolong the life of animals with liver cancer;

II. Hepatic arterial injection or single liver tumor injection with radioactive arsenic trioxide can cause immediate damage to the tumors so as to inhibit tumor growth, thereby resulting in shrinkage and disappearance; the therapeutic effect of hepatic arterial injection or single liver tumor injection with non-radioactive arsenic trioxide is inferior; and III. The dosage of radiation absorption by the liver tumors in the animal bodies injected with radioactive arsenic trioxide via the hepatic artery is five times that when injected via the tail vein.

While the present invention has been described in connection with what is considered the most practical and preferred embodiment(s), it is understood that this invention is not limited to the disclosed embodiment(s) but is intended to cover various arrangements included within the spirit and scope of the broadest interpretations and equivalents.

We claim:

1. A method for treating a subject having a tumor or cancer, comprising the step of administering to the subject a radioactive arsenic-containing compound prepared by a process comprising the steps of:

subjecting an arsenic-containing compound selected from the group consisting of $As_2O_3$, $As_2S_3$, $As_2S_2$, and combinations thereof, to a neutron irradiation treatment such that the arsenic element contained in said arsenic-containing compound is converted to a radioactive arsenic isotope, wherein said radioactive arsenic isotope is $^{76}As$; and (ii) recovering the resultant product from step (i).

2. The method according to claim 1, wherein the tumor or cancer is a solid tumor.

3. The method according to claim 2, wherein the solid tumor is selected from the group consisting of breast cancer, rectal cancer, liver tumor, ovarian cancer and prostate cancer.

4. The method according to claim 3, wherein the liver tumor is selected from the group consisting of hepatocellular carcinoma, cholangiocarcinoma, liver cell carcinoma, fibrolamellar variant of hepatocellular carcinoma, intrahepatic bile duct carcinoma, mixed hepatocellular cholangicocarinomoa, undifferentiated hepatocellular carcinoma, hepatoma with tumor invasion to common bile duct, hepatoblastoma, childhood hepatic tumor and primary hepatocellular carcinoma.

5. The method according to claim 1, wherein said radioactive arsenic-containing compound emits γ particles and β particles.

6. The method according to claim 1, wherein said radioactive arsenic-containing compound is $As_2O_3$ subjected to the neutron irradiation treatment.

7. The method according to claim 1, wherein administering said radioactive arsenic-containing compound to the subject is conducted via injection.

8. The method according to claim 1, wherein said radioactive arsenic-containing compound is formulated together with a pharmaceutically acceptable carrier.

9. The method according to claim 8, wherein the pharmaceutically acceptable carrier is selected from a group consisting of water, normal saline, glycerol, organic solvents, stabilizers, chelating agents, preservatives, emulsifiers, suspending agents, diluents, gelatinizers, and liposomes.

10. A pharmaceutical composition for treating a tumor or cancer, comprising:
   (a) a therapeutically effective amount of a radioactive arsenic-containing compound said radioactive arsenic isotope is $^{76}As$ prepared by the steps of:
      (i) subjecting an arsenic-containing compound selected from the group consisting of $As_2O_3$, $As_2S_3$, $As_2S_2$, and combinations thereof, to a neutron irradiation treatment such that the arsenic element contained in said arsenic-containing compound is converted to a radioactive arsenic isotope; and
      (ii) recovering the resultant product from step (i); and
   (b) a pharmaceutically acceptable carrier.

11. The pharmaceutical composition according to claim 10, which is formulated into an injection formulation.

12. The pharmaceutical composition according to claim 10, wherein said radioactive arsenic-containing compound emits γ particles and β particles.

13. The pharmaceutical composition according to claim 10, wherein said radioactive arsenic-containing compound is $As_2O_3$ having been subjected to the neutron irradiation treatment.

* * * * *